United States Patent
Dyadischev et al.

(10) Patent No.: US 6,287,842 B1
(45) Date of Patent: Sep. 11, 2001

(54) STRAIN OF ALCALIGENES LATUS BACTERIA USED FOR THE DECOMPOSITION OF POLYCHLORINATED BIPHENYLS

(75) Inventors: Nikolai Romanovich Dyadischev; Gennady Alekseevich Zharikov; Vladimir Vladimirovich Kapranov, all of Moscow Region (RU)

(73) Assignee: Research Center for Toxicology and Hygienic Regulatiom of Biopreparation, Moscow Region (RU)

( * ) Notice: Subject to any disclaimer, the term of this patent is extended or adjusted under 35 U.S.C. 154(b) by 0 days.

(21) Appl. No.: 09/601,510

(22) PCT Filed: Feb. 13, 1998

(86) PCT No.: PCT/RU98/00036

§ 371 Date: Sep. 20, 2000

§ 102(e) Date: Sep. 20, 2000

(87) PCT Pub. No.: WO99/41356

PCT Pub. Date: Aug. 19, 1999

(51) Int. Cl.[7] .................................. C12N 1/12; B09B 3/00
(52) U.S. Cl. .................................... 435/252.1; 435/262.5; 435/829
(58) Field of Search ............................ 435/262.5, 252.1, 435/829

(56) References Cited

U.S. PATENT DOCUMENTS

| | | | |
|---|---|---|---|
| 4,843,007 | * 6/1989 | Berdard et al. | 435/252.1 |
| 4,876,201 | * 10/1989 | Bedard et al. | 435/829 |
| 5,024,949 | * 6/1991 | Hegeman et al. | 435/262 |
| 5,516,688 | 5/1996 | Rothmel | 435/262.5 |
| 5,945,331 | * 8/1999 | Kozaki et al. | 435/262.5 |
| 5,962,305 | * 10/1999 | Mihara et al. | 435/262.5 |

OTHER PUBLICATIONS

Zharikov G.A., Dyadischeva V.P., "Evaluation of integrated soil toxicity by biotesting", abstract from presentation at conference "Ecological Protection of Towns", Moscow, 1996, pp. 222–223.

Zharikov G.A., Borovick R.V., "Integrated system for soil recultivation by biotechnological methods", Toksikologicheskiy Vestnik, 1996, N3, pp. 23–24.

Borovick R.W., Djadischev N.R., Zharikov G.A., Die toxikologischen und vorklinischen Forschyngen der immunobiologischen Praparate in RuBland, presentation at Medical B–protection Conference (Munchen, 1996), Muchen, 1996, S.26.

Zharikov G.A., Kapranov V.V., Borovick R.V., Dyadischev N.R., "Development of biotechnology of intensive remediation of soil polluted with polphenyls", Abstract from presentation at scientific–technical seminar "Protection of environment from industrial and agricultural pollutions", Athens Greece, 1997, pp.48–49.

Marchenko A.I., Zharikov G.A., Kapranov V.V., Vorob'iev A.V., Dyasichev N.R., Borovick R.V., "Influence of polychlorinated biphenyls (PCBs) on biological state of soddy soils", Abstract from presentation at scientific–technical seminar "Protection of environment from industrial and agricultural pollutions", Athens Greece, 1997, pp.50–51.

Rybalkin S.P., Dyadischev N.R., Goltsev I.A., "Toxic effects of chemical soil pollutants and polyphenyls for warm–blooded animals after their penetration into organism with drinking water",7 Abstract from presentation at scientific–technical seminar "Protection of environment from industrial and agricultural pollutions", Athens, Greece, 1997, pp. 52–52.

Zharikov G.A., Dyadischeva V.P., Dyadischev N.R., Rybalkin S.P., "Application of biotesting for evaluation of integrated toxicity of soils and dust–heaps", Abstract from presentation at scientific–technical seminar "Protection of environment from industrial and agricultural pollutions", Athens, Greece,1997, pp.59–60.

Marchenko A.I., Rybalkin S.P., Vorb'iev A.V., Zhukov S.I., Dyadischev N.R., "Establishment of correlation links between toxicity of nonorganic compositions in animals and culture test–models", Athens, Greece, 1997, pp. 61–62.

Kapranov V.V., Zharikov G.A., Uspenskaya S.N., Dyadischev N.R., "Application of microorganisms–biodegraders for remediation of soil polluted with polychlorinated biphenyls",Abstract for presentation at International Sc.–Pract. Conference, Apr. 15–17, 1997, Penza ,pp.170–172.

Document B10, Zharikov G.A., Dyadischeva V.P., "Biological method for evaluation of integrated soil toxicity", Abstract for presentation at International Sc.–Pract. Conference, Apr. 15–17, 1997, Penza, pp. 173–174.

Zharikov G.A., Marchenko A.I., Rybalkin S.P., Kapranov V.V., Dyadischev N.R., Borovick R.V., Study of toxic effect of polyphenyls on biological soil activity, Toksikologicheskiy Vestnik, 1997, in press.

Zharikov G.A., Borovick R.V., Dyadischev N.R., Kapranov V.V., Kiselyoa N.I., Dyadischeva V.P., Aldobaev V.N., "Development of Biotechnology for Detoxification of Soils Polluted with Polyphenyls", Symposium "Dioxin 97", U.S.A., Indianapolis, Aug. 25–29, 1997.

(List continued on next page.)

Primary Examiner—Herbert J. Lilling
(74) Attorney, Agent, or Firm—Randall W. Chang; William C. Daubepspeck; Paul A. Gottlieb

(57) ABSTRACT

Alcaligenes latus bacterial strain TXD-13 VKPM B 75-05 is capable of degrading polychlorinated biphenyls (PCBs). The strain may be employed to detoxicate environment media and PCB-containing industrial waste. To produce biomass, the strain is incubated on media which contain carbon sources, nitrogen sources and mineral salts. The strain is cultivated by a subsurface method up to a titer from $6.0 \cdot 10^8$ to $2.0 \times 10^9$ cells per cu cm. The produced biomass is used for degrading PCBs in concentrations from $10^7$ to $10^8$ cells per cu cm. The strain ensures from 35 to 50% reduction in PCB content in soil and water.

1 Claim, No Drawings

OTHER PUBLICATIONS

Rybalkin S.P., Dyadischev N.R., Goltsev I.A., Bodrova N.V., Buziun A.V., "Combined Effect of Soil Chemical Pollutants and Polyphenyls After Their Penetration With Drinking Water Into Organism of Warm Blooded Animals", Symposium "Dioxin 97", U.S.A., Indianapolis, Aug. 25–29, 1997.

Zharikov G.A., Borovick R.V., Kiselyov N.I., Aldobaev V.N., "Application of Biological Sorbents for Treatments of Soils Polluted by Heavy Metals and Radionuclides", Acta Entomologica Bulgarica, 1997, vol. 3, No. 1–2, pp. 129–132.

Zharikov G.A., Kiselyova N.I., Kapranov V.V., Aldobaev V.N., Borovick R.V., Dyadischev N.R., "Study of the Possibilities to Employ Earthworms, Biosorbents and biohumus for treatment of soils polluted by Heavy Metals and Radionuclides", International Conference Migration of HM and RN in the chain Soil–Plant–Animal–animal husbandry production–Human, (Novgorod, Mar. 23–25, 1998) –Novgorod 1998, pp. 146–149.

Zharikov G.A., Kiselyova N.I., Kapranov V.V., Aldobaev V.N., Borovick R.V., Dyadischev N.R., "Study of the possibility to employ earthworms and biosorbents to soils contaminated by RN", Proceedings from Seminar "Ecological aspects of storage, Processing and use of by products", (Lousanna, Switzerland, May 26–31, 1998), Moscow, 1998, pp. 24–25.

Zharikov G.A., Kapranov V.V., Rybalkin S.P., Borovick R.V., Dyadischev N.R., "Taking Advantage of microorganisms–degraders for remediation of soils polluted by PCBs", Proceedings from Seminar "Ecological aspects of storage, Processing and use of by products", (Lousanna, Switzerland, May 26–31, 1998), Moscow, 1998, pp. 26–27.

Marchenko A.I., Rybalkin S.P., Zharikov G.A., Dyadischev N.R., Borovick R.V., "Study of accumulating process for gentoxic compounds in soddy soils polluted by PCB", Proceedings from Seminar "Ecological aspects of storage, Processing and use of by products", (Lousanna, Switzerland, May 26–31, 1998), Moscow, 1998, pg. 28.

Dyadischev N.R., Rybalkin S.P., Onatsky N.M., Marchenko A.I., Zharikov G.A., Kapronov V.V., "Toxicological assessment of biological method effciency for remediation of soils polluted by PCBs", Proceedings from Seminar "Ecological aspects of storage, Processing and use of by products", (Lousanna, Switzerland, May 26–31, 1998), Moscow, 1998, pg. 29.

Zharikov G.A., Borovick R.V., Dydischev N.R., Kapranov V.V., Kiselyova N.I., Dyadischeva V.P., Rybalkin S.P., "Ecologically safe Technology for Bioremediation of Soils polluted by toxic chemical substances", abstract from presentation at Workshop "Environmental Aspects Converting CW Facilities to Peaceful Purpose and Derivative Technologies in Modeling, Medicine and Monitoring", Spiz, Switzerland, Mar. 7–10, 1999.

Zharikov G.A., Borovick R.V., Dydischev N.R., Kapranov V.V., Kiselyova N.I., Dyadischeva V.P., Rybalkin S.P., Aldobaev V.N., and Marchenk A.I., "Ecologically Safe Biotechnologies for Processing Industrial Organic Wastes and Bioremediation of Soils Polluted by Toxic Chemical Substances and Radioluclids", Poster paper at the German––Russian Workshop of Biotechlogitst and at the Conference "DECHEMA", Wiesbaden, Germany, Apr. 26–29, 1999.

Zharikov G.A., Borovick R.V., Dyadischev N.R., Kapranov V.V., Kovalyov V.P., Kovalyova N.I., Dyadischeva V.P., Rybalkin S.P., "Bioremediation of Soils Polluted by Toxic Chemical Substances and Radionuclides", Contaminated Soil 2000 conference, Leipzig, Germany, Sep. 18–22, 2000.

Varenik V.I., Borovick R.V., "Bioremediation of Soils Polluted by Toxic Chemical Substances", Promising Research Abstract #PRA2124, available on worldwide web May 31,1999.

Zharikov G.A., "Development of Biotechnology for Intensive Detoxication of Soils Polluted by Polychlorinated Biphenyls", ISTC #228 Project summary, May 1999.

Boyle,M., "the Environmental Microbiology of Chlorinated Aromatic Decomposition", Journal of Environmental Quality, vol. 18, Oct.–Dec. 1989, Number 4, discusses the use of alcaligenes for the degradation of PCB's.

* cited by examiner

STRAIN OF ALCALIGENES LATUS BACTERIA USED FOR THE DECOMPOSITION OF POLYCHLORINATED BIPHENYLS

This application is a 371 of PCT/RU98/00036 filed Feb. 13, 1998.

FIELD OF THE INVENTION

The present invention relates to biotechnology and provides a new bacterial strain which is able to degrade polychlorinated biphenyls (PBCs) under aerobic conditions in situ in environment media.

Introduction of chemical advances into industry and household involves many hazards of immediate and long-term chemical impact. As of now, the issue of environment pollution control has become extremely pressing.

BACKGROUND OF THE INVENTON

PCBs have been manufactured since 30th and found application for the most part in electrical industry. By late 60th, it has turned out that the environment contained from 300 to 500 thousand tons PCBs (Tarasov V. V. Contamination of the Environment with Polychlorinated Biphenyls and Ways for Minimizing Their Impact, Collection of Scientific Works of RKhTY LXXV Years/Main Scientific Achievements. Moscow, 1996, p.24–41). Annual release of PCBs averages 2000 tons. PCBs penetrate into the environment as the result of failures of PCB-containing equipment and systems, and due to incineration. PCBs penetration into soil is caused by equipment failures or discharges of untreated industrial sewage from plants that employ PCBs in their production run, and by utilization of sludge from irrigated fields. Owing to high absorption power and low degradation ability, polychlorinated biphenyls accumulate in the soil surface layer at a depth of 2–10 cm and in bed sediments. PCBs have been detected substantially in all living nature. PCB is a polytropic poison which affects essentially all body organs and systems. According to data published by the WHO, a human appears to be the most PCB-sensitive creature. PCBs relate to substances of the first hazard group.

Worldwide practice for remediating environment media from PCBs is to use, in general, various physical and chemical methods. In Germany, PCB-contaminated soil is remediated by a method developed by National Research, Canada. According to the method, special dispersion sodium-oil blends are introduced into old landfill sites to assist in chlorine release from PCBs with formation of common salt. (Deckwer W.-D. Weppen P. Review of Methods for Remediating Contaminated Soil and Refused Territories Contaminated with Hazardous Waste.—Chemie-Ingenieur-Technik, 1987, Vol.59, #6, p.457–467).

Gebruder Kemmer/Jng Buro Harbauer Group (Germany) has invented a method for remediation of PCB-contaminated soil, which involves excavation of the soil. The method includes crushing and sieving the soil, the obtained fractions being separately decontaminated with water to which surfactants are added. Flush liquid is supplied to a sewage treatment plant (Schondorf T., Munz K. H. Removal of Polychlorinated Biphenyls from Contaminated Soil.—Chem.Rosch. (Schweiz.), 1988, v.41, #45, s.18).

Kloeckner Oecotec GmbH, Germany, has invented a method for remediation of PCB-contaminated soil, involving washing the soil under a high pressure at a pilot plant. The soil in the form of pieces of up to 10 mm in diameter is ground in a conical water jet. A high pressure of 250 bar in an annular pipe and a great rate of 200–250 m/s promote a complete homogenization and separation of the smallest components and hazardous substances. After the water treatment of the soil, the suspension is separated by one of the following methods: precipitation, cyclone separation, centrifugation, filtration, etc.

Developed in Russia are methods for soil decontamination from PCBs with the aid of a propulsion, plasmatrons (Tarasov V. V. Contamination of the Environment with Polychlorinated Biphenyls and Ways of Minimizing Their Impact. Collection of Scientific Works of RKhTY LXXV years/ Main Scientific Achievements, Moscow, 1996, p.24–41).

All of the above methods suffer a number of essential problems: they are cumbersome, require great investments and disturb the soil ecological equilibrium.

Since late 70th, an ever increasing interest has been expressed in bioremediation methods. It is well known that various bacterial strains and fungi are able to degrade PCBs. They include microorganisms of Pseudomonas genus (*Pseudomonas putide* for degrading poly-chlorinated biphenyls. U.S. Pat. No. 4843009, Int.Cl. C12N 1/12 Application No.866501 filed on May 23, 1986) and fungi of Whit Rod Fungus *Phanerochaete chrysosporium* (Degradation of 4',4'-Dichlorobiphenyl, 3,Y,4,4'-Tetrachlorobiphenyl, and 2,2',4,4',5,5'-Hexachlorobiphenyl by the White Rot Fungus *Phanerochaele chrysosporium*. Applied and Environmental Microbiology. 1995. Vol.61, N.11, p.3904–3909), however, the bacteria of Pseudomonas genus are fastidious to nutrient media and storage conditions. Fungi are less convenient in production, and they cause, among other things, a shift in the ecological equilibrium when employed in environment media.

SUMMARY OF THE INVENTION

It is an object of the invention to isolate a new microorganism strain which is capable of degrading greater PCB concentrations in environment media in situ under aerobic conditions, and which is convenient in production and employment.

*Alcaligenes latus* bacterial strain TXD-13 has been isolated from soil and selected as the result of long-term subculturing of separate bacterial colonies on a minimal salts medium (Practicum in Microbiology, M., MGU Publishers, 1976) containing

| | |
|---|---|
| $(NH_4)_2HPO_4$ | 1.5 g |
| $KH_2PO_4$ | 0.7 g |
| NaCl | 0.5 g |
| $Mg_2SO_4$ | 0.8 g |
| distilled water | up to 1 liter |
| pH | 7.2 | in the presence of different PCB concentrations, from 100 to 400 mg per a liter of a nutrient medium.

The strain was selected by a PCB degradation level and velocity, and by its genetic PCB-resistance.

Genetic resistance of selected strains was attained by repeated subculturing on dense nutrient media. Colonies grown on them were then subcultured on a minimal salts medium having the above composition.

As the result, a new genetically resistant bacterial strain of *Alcaligenes latus* TXD-13 has been obtained. Identification was made in accordance with the Bergey identifier. The strain, (identified as Alcaligenes latus TDX-13), was deposited on Feb. 12, 1997, under the terms of the Budapest Treaty with the Russian National Collection of Industrial Microorganisms (Vserossiskaya kollektsiya promyshlennykh microorganismov, abbreviated as VKPM), and has the accession deposit number of VKPM B-7505. The address of VKPM is: Russian National Collection of Industrial Microorganisms (VKPM), GNII genetika, Dorozhny proezd. 1, Moscow 113545, Russian Federation.

The strain features the following culture, morphological, physiological and biochemical characters.

Culture and morphological characters.

On a glucose/peptone medium plus a yeast extract, the strain forms clear colonies, their surface changing from bright to opaque with age. The colonies are greyish in color, changing to yellowish. When subcultured, the colonies are 2–3 mm in diameter.

On the Endo, Ploskirev medium, the culture grows in the form of smooth bright colonies. The culture is gram-negative with a smear containing small rods and cocci. In a liquid nutrient medium the culture grows at a temperature of 29° C. during 72 hours at an agitator rotation speed of 200 rev/min.

Physiological characters

The culture is aerobic, grows at a temperature from +4° C., does not grow at a temperature of +37° C., the optimal temperature being +20° C. Grows on media with pH 6.0–8.0, optimal pH 6.8–7.5. Grows on rich nutrient media based on a meat infusion broth (MIB) and enzymic fish flour digest (EFFD).

Biochemical characters

In the Smith media, the culture assimilates glycerol, fructose, D-glucose as a sole carbon source. The culture is catalase-positive and oxidase-positive. Uses nitrogen of organic and inorganic origin.

Storage media: EFFD or MIB and minimal salts media with PCB.

To produce bacterial biomass for degrading PCB, the strain may be incubated on various nutrient media containing common carbon and nitrogen sources, mineral salts.

Carbon sources which can be used in the practice of the present invention are PCB, glucose, fructose, glycerol. Nitrogen sources can be both organic and inorganic substances. Organic nitrogen sources can be EFFD, peptone, yeast autolysate, corn extract, etc. Inorganic nitrogen sources are nitrates.

The invention will be further explained by the following examples.

EXAMPLE 1

Production of strain biomass.

*Alcaligenes lalus* bacterial strain TXD-13 was incubated under aerobic conditions on a liquid MIB-based nutrient medium by a subsurface method at temperature t=29±2° C. and an agitator rotational speed of 200 rev/min for 72 hours. A titer of the incubated culture was $2.0 \times 10^9$ cells per cu cm.

EXAMPLE 2

Soil remediation under laboratory conditions.

Different PCB concentrations were introduced into a soil sample, followed by vigorous agitation of the sample. The obtained culture liquid was diluted with pipeline water up to a titer of $10^8$–$10^7$–$10^6$ cells per cu cm. The cell suspension was sprayed onto a surface of the PCB-contaminated soil in the amount of a liter per sq. m. The soil was held at a room temperature for two months. Test samples were taken after 0.5, 1 and 2 months.

PCB concentration in the treated soil was determined on a "Crystal" gas-liquid chromatograph in accordance with a method disclosed in Methods for Determining Pesticide Microqualities in Food, Feedstuff and the Environment. T.2.M.—Agropromizdat.-1992, p.p.143–148. PCB was extracted from the soil sample by hexane and introduced into the gas-liquid chromatograph equipped with an electron capture detector. Analysis results are summarized in Table 1.

TABLE 1

Dynamics of PCB degradation in soil as a function of cell concentration in a suspension

| Cell concentration in suspension (cells per cu cm) | Time (months) | PCB concentration (mg/kg) | | |
|---|---|---|---|---|
| | initial PCB concentration | 32.6 | 49.0 | 70.2 |
| $10^6$ | 0.5 | 20.3 | 17.6 | 42.8 |
| | 1 | 15.2 | 15.1 | 30.3 |
| | 2 | 8.5 | 7.7 | 18.9 |
| $10^5$ | 0.5 | 22.1 | 17.9 | 54.8 |
| | 1 | 11.6 | 10.3 | 29.4 |
| | 2 | 20.7 | 34.8 | 28.3 |
| $10^4$ | 0.5 | 28.5 | 28.1 | 55.7 |
| | 1 | 15.3 | 7.6 | 41.0 |
| | 2 | 10.4 | 10.2 | 42.9 |

As may be seen from Table 1, the most optimal cell concentration in a suspension to be introduced into soil is $10^7$ cells per cu cm, while a cell concentration of $10^6$ cells per cu cm appears ineffective.

A concentration of $10^8$ cells per cu cm in a suspension to be introduced into soil is unprofitable.

EXAMPLE 3

Soil remediation in situ

A cell suspension prepared as in Example 1 was sprayed onto a soil surface with the aid of a backpack sprayer in the amount of a liter per sq. m. Upon introduction of the suspension, the soil was carefully dug and held at ambient temperature for 2 months. Analysis was conducted as in the previous example.

Test samples were taken during a first and second month.

Analysis results are summarized in Table 2.

TABLE 2

PCB degradation in situ

| Test time | Control | first month | second month |
|---|---|---|---|
| PCB content in soil (mg/kg) | 49.0 | 43.7 | 10.8 |

As will be seen from the data above, PCB concentration in soil samples was reduced by 45.3% within 2 months.

EXAMPLE 4

Water decontamination

A cell suspension prepared as in Example 1 was added to 5 liters of sewage containing 25 mg/l PCB. The suspension was introduced in the amount of $10^7$ cells per liter. Upon introduction of the suspension, the water was agitated at a speed of 10 rev/min during 14 days at a room temperature.

Water samples for analysis were taken after one and two weeks and analyzed as in the previous example.

The analysis results are presented in Table 3.

TABLE 3

PCB degradation in water

| Test time | control | first week | second week |
|---|---|---|---|
| PCB content in water (mg/kg) | 25.0 | 12.9 | 6.1 |

As may be seen from the above data, PCB concentration in sewage was reduced by 40% within 2 weeks.

INDUSTRIAL APPLICABILITY

The strain in accordance with the invention ensures approximately 50% reduction in PCB concentration in environment media. The strain is applicable to detoxicate environment media, in particular, soil, water and PCB-containing waste of electrical and chemical industry.

In prospect, the strain may be employed to produce various organic compounds from PCBs and PCB-containing waste.

What is claimed is:

1. *Alcaligenes latus* bacterial strain VKPM B 75–05 for degrading polychlorinated biphenyls.

* * * * *